(12) United States Patent
Xie et al.

(10) Patent No.: US 11,737,998 B2
(45) Date of Patent: Aug. 29, 2023

(54) COMPOSITION FOR TREATING BURN WOUNDS

(71) Applicant: Yan Xie, Ningxia (CN)

(72) Inventors: Yan Xie, Ningxia (CN); Yinsheng Wu, Ningxia (CN); Guangyu Guan, Ningxia (CN); Qian Chen, Henan (CN); Dan Zhao, Ningxia (CN); Jingjing An, Ningxia (CN)

(73) Assignee: Yan Xie, Ningxia (CN)

( * ) Notice: Subject to any disclaimer, the term of this patent is extended or adjusted under 35 U.S.C. 154(b) by 39 days.

(21) Appl. No.: 17/180,965

(22) Filed: Feb. 22, 2021

(65) Prior Publication Data
US 2021/0401786 A1  Dec. 30, 2021

(30) Foreign Application Priority Data
Jun. 24, 2020 (CN) .......................... 202010591188.7

(51) Int. Cl.
| | | |
|---|---|---|
| A61K 31/198 | (2006.01) | |
| A61P 17/02 | (2006.01) | |
| A61K 31/201 | (2006.01) | |
| A61K 31/216 | (2006.01) | |
| A61K 31/355 | (2006.01) | |
| A61K 31/401 | (2006.01) | |
| A61K 31/4172 | (2006.01) | |
| A61K 31/7048 | (2006.01) | |
| A61K 33/06 | (2006.01) | |
| A61K 33/42 | (2006.01) | |
| A61K 45/06 | (2006.01) | |

(52) U.S. Cl.
CPC .......... *A61K 31/198* (2013.01); *A61K 31/201* (2013.01); *A61K 31/216* (2013.01); *A61K 31/355* (2013.01); *A61K 31/401* (2013.01); *A61K 31/4172* (2013.01); *A61K 31/7048* (2013.01); *A61K 33/06* (2013.01); *A61K 33/42* (2013.01); *A61K 45/06* (2013.01); *A61P 17/02* (2018.01)

(58) Field of Classification Search
CPC .. A61K 31/198; A61K 31/201; A61K 31/216; A61K 31/355; A61K 31/401; A61K 31/4172; A61K 31/7048; A61K 33/06; A61K 33/42; A61K 45/06; A61K 31/19; A61K 31/192; A61K 31/20; A61K 31/202; A61K 31/351; A61K 31/352; A61K 31/37; A61K 31/4178; A61K 31/4375; A61K 31/4748; A61K 31/7004; A61K 31/7036; A61K 31/7076; A61K 38/14; A61K 31/12; A61K 31/137; A61K 31/165; A61K 31/194; A61K 31/365; A61K 31/366; A61K 31/405; A61K 31/437; A61K 31/522; A61K 31/5685; A61K 31/58; A61K 33/26; A61K 33/30; A61K 33/34; A61K 38/12; A61P 17/02
See application file for complete search history.

(56) References Cited

U.S. PATENT DOCUMENTS

| | | | | |
|---|---|---|---|---|
| 4,857,328 A | * | 8/1989 | Trenzeluk | A61Q 19/00 514/762 |
| 2011/0165276 A1 | * | 7/2011 | Coley | A61P 17/02 424/744 |
| 2016/0243164 A1 | * | 8/2016 | Yates | A61K 33/38 |

FOREIGN PATENT DOCUMENTS

| | | |
|---|---|---|
| CN | 1771930 A | 5/2006 |
| CN | 101129787 A | 2/2008 |
| CN | 101953859 A | 1/2011 |
| CN | 110448581 A | 11/2019 |

OTHER PUBLICATIONS

Hamman, J. Composition and Applications of Aloe vera Leaf Gel. Molecules, 13(8), 1599-1616. Published Aug. 2008. (Year: 2008).*
First Office Action dated Jan. 20, 2023 in corresponding Chinese Patent Application No. 202010591188.7 filed Jun. 24, 2020 (8 pages) with Google machine translation (3 pages).

* cited by examiner

Primary Examiner — Brandon J Fetterolf
Assistant Examiner — Lauren Wells
(74) Attorney, Agent, or Firm — Daniel F. Nesbitt; Nesbitt IP LLC (57) ABSTRACT

A composition for treating a burn wound, containing a variety of ingredients, including a fatty acid 261-639 mg, an organic substance 3.5-350 mg, a carbohydrate 0.02-60 mg, a vitamin 9-13 µg, a microelement 3.04-5.5 mg, an antibiotic 0.6-70 mg, and an amino acid 105-335 mg. The significant therapeutic effects include effectively promoting repair of a burn wound, anti-infection, inhibiting scar hyperplasia, no toxic side effect, convenient use, fast absorption, economical efficiency, etc. The composition provides patients with an efficient, economical, convenient and practical treatment for burn wounds, which greatly reduces the burden on patients, and effectively compensates for the various deficiencies of the current treatments for the non-healing burn wounds.

13 Claims, 5 Drawing Sheets

COMPOSITION FOR TREATING BURN WOUNDS

CROSS-REFERENCE TO RELATED APPLICATION

This application claims the benefit of priority to the Chinese patent application No. CN202010591188.7, filed with the China National Intellectual Property Administration on Jun. 24, 2020, entitled "A mixture for treating burn wounds", the disclosure of which is incorporated herein by reference.

FIELD OF THE INVENTION

The invention relates to the field of medical technology, in particular to a composition for treating a burn wound.

BACKGROUND OF THE INVENTION

A burn is an injury to a skin or other tissue or organ, which is mostly caused by high temperature, radiation, electricity, friction, or exposure to chemicals. According to a recent report from the World Health Organization, the burn is a global public health problem. Statistics suggest that there are about 10 million burn patients, resulting in about 265,000 deaths worldwide every year, most of which occur in low- or middle-income countries. In India, more than 1 million people suffer from moderate or severe burns every year. A scar is one of the sequelae of the burn with an incidence of 91.4%. The annual cost estimate for treating scars is at least 4 billion dollars per year. The burn leads to heavy economic burdens to the state and the society. A non-lethal burn, such as a non-healing burn wound, also cause huge mental trauma, physical pain, and heavy economic burdens to the patients.

The non-healing burn wound frequently occurs over a long period of time after a burn injury, carrying a risk of relapse and carcinogenesis. It remains a difficult problem to develop a treatment for the non-healing burn wound suitable for clinic use, which is also important for the research in the field of burns. A novel therapy for treating a non-healing burn wound is urgently needed to solve the above problem.

SUMMARY OF THE INVENTION

This application provides a composition for treating a burn wound.

The first aspect of the application provides a composition for treating a burn wound, including the following ingredients in mass content: a fatty acid 261-639 mg, an organic substance 3.5-350 mg, a carbohydrate 0.02-60 mg, a vitamin 9-13 µg, a microelement 3.04-5.5 mg, an antibiotic 0.6-70 mg, and an amino acid 105-335 mg.

The second aspect of the application provides a composition for treating a burn wound, which is recorded in parts by weight and includes the following ingredients: 261-639 parts of fatty acid, 3.5-350 parts of organic substance, 0.02-60 parts of carbohydrate, 0.009-0.013 parts of vitamin E, 3.04-5.5 part of microelement, 0.6-70 parts of antibiotic, 105-335 parts of amino acid;
wherein,
the fatty acid is at least one selected from the group consisting of oleic acid, linoleic acid, linolenic acid and palmitic acid;
the organic substance is at least one selected from the group consisting of ellagic acid, hypaphorine, huperzine C, huperzine A, harmalol, abrine, berberine hydrochloride, 10-gingerol, methyl gallate, spathulenol, 3-furylmethyl 1H-pyrrole-2-carboxylate, tanshinone, dihydrocapsaicin, potassium 7-hydroxy-1-naphthalenesulfonate, pilocarpine, adenosine, firmanoic acid, glabrolide, liquidambaric lactone, schisandrolactone, dehydroepiandrosterone, 11(13)-dehydroivaxillin, 2-hydroxyeupatolide, 14,15beta-dihydroxyklaineanone, olaquindox, oridonin, phorbol, harmine, maltol, hypoaconitine, 2-O-Rhamnosylicariside II, theobromine, theophylline, hordenine, ephedrine;
the carbohydrate is at least one selected from the group consisting of fructose and glucose;
the microelement is at least one selected from the group consisting of calcium, iron, zinc, copper, and phosphorus;
the antibiotic is at least one selected from the group consisting of mupirocin, neomycin, polymyxin B, gentamicin, amphotericin B and vancomycin; and
the amino acid is at least one selected from the group consisting of glutamic acid, arginine, aspartic acid, serine, glycine, alanine, tyrosine, histidine, proline, cysteine, valine, isoleucine, leucine, phenylalanine, methionine, threonine, and lysine.

In some embodiments of the second aspect of the present application, the fatty acid also include at least one selected from the group consisting of stearic acid, butyric acid, hexanoic acid, octanoic acid, myristic acid, palmitoleic acid, heptadecanoic acid, eicosanoic acid, and cis-11-eicosenoic acid; wherein, in parts by weight, the total content of the oleic acid, linoleic acid, palmitic acid and linolenic acid is not less than 250 parts.

In some embodiments of the second aspect of the present application, in parts by weight, the fatty acid include: 20-50 parts of palmitic acid, 10-30 parts of stearic acid, 100-200 parts of oleic acid, 100-300 parts of linoleic acid, 30-50 parts of linolenic acid, 0.1-1 parts of butyric acid, 0.1-1 parts of hexanoic acid, 0.1-1 parts of octanoic acid, 0.1-1 parts of myristic acid, 0.1-1 parts of palmitoleic acid, 0.1-1 parts of heptadecanoic acid, 0.1-1 parts of eicosanoic acid and 0.3-2 parts of cis-11-eicosaenoic acid.

In some embodiments of the second aspect of the present application, in parts by weight, the organic substance include: 0.1-10 parts of ellagic acid, 0.1-10 parts of hypaphorine, 0.1-10 parts of huperzine C, 0.1-10 parts of huperzine A, 0.1-10 parts of harmine, 0.1-10 parts of abrine, 0.1-10 parts of berberine hydrochloride, 0.1-10 parts of 10-gingerol, 0.1-10 parts of methyl gallate, 0.1-10 parts of spathulenol, 0.1-10 parts of 3-furylmethyl 1H-pyrrole-2-carboxylate, 0.1-10 parts of tanshinone, 0.1-10 parts of dihydrocapsaicin, 0.1-10 parts of potassium 7-hydroxy-1-naphthalenesulfonate, 0.1-10 parts of pilocarpine, 0.1-10 parts of adenosine, 0.1-10 parts of firmanoic acid, 0.1-10 parts of glabrolide, 0.1-10 parts of liquidambaric lactone, 0.1-10 parts of schisandrin, 0.1-10 parts of dehydroepiandrosterone, 0.1-10 parts of 11(13)-dehydroivaxillin, 0.1-10 parts of 2-hydroxyzeranolide, 0.1-10 parts of 14,15beta-dihydroxyklaineanone, 0.1-10 parts of olaquindox, 0.1-10 parts of oridonin, 0.1-10 parts of phorbol, 0.1-10 parts of harmine, 0.1-10 parts of maltol, 0.1-10 parts of hypaconine, 0.1-10 parts of 2-O-rhamnosylicariside II, 0.1-10 parts of theobromine, 0.1-10 parts of theophylline, 0.1-10 parts of hordeine and 0.1-10 parts of ephedrine.

In some embodiments of the second aspect of the present application, in parts by weight, the carbohydrate include 0.01-30 parts of glucose and 0.01-30 parts of fructose.

In some embodiments of the second aspect of the present application, in parts by weight, the microelement include:

0.5-1 parts of calcium, 0.01-0.1 parts of iron, 0.02-0.2 parts of zinc, 0.01-0.2 parts of copper, 2.5-4s part of phosphorus.

In some embodiments of the second aspect of the present application, in parts by weight, the antibiotic include: 0.1-20 parts of mupirocin, 0.1-10 parts of neomycin, 0.1-10 parts of polymyxin B, 0.1-10 parts of gentamicin, 0.1-10 parts of amphotericin B and 0.1-10 parts of vancomycin.

In some embodiments of the second aspect of the present application, in parts by weight, the amino acid include: 20-50 parts of glutamic acid, 20-40 parts of arginine, 10-30 parts of aspartic acid, 5-20 parts of serine, 5-20 parts glycine, 5-20 parts of alanine, 5-20 parts of tyrosine, 1-10 parts of histidine, 1-10 parts of proline, 1-10 parts of cysteine, 5-10 parts of valine, 5-10 parts of isoleucine, 10-30 parts of leucine, 5-20 parts of phenylalanine, 1-5 parts of methionine, 2-15 parts of threonine and 4-15 parts of lysine.

The significant therapeutic effects of the composition for treating a burn wound provided in the present invention include effectively promoting the repair of the non-healing burn wound, anti-infection, inhibiting scar hyperplasia, no toxic side effect, convenient use, fast absorption, economical efficiency, etc. The application provides the patients with an efficient, economical, convenient and practical treatment for non-healing burn wounds, which greatly reduces the burden on patients, and effectively compensates for the various deficiencies of the current treatments for the non-healing burn wounds.

DESCRIPTION OF THE DRAWINGS

In order to explain more clearly the Examples of the present invention and the technical solutions in the art, the drawings used in the Examples and the prior art are briefly described below. It is obvious for those skilled in the art that the following drawings are only some embodiments of the present invention, from which other drawings can be obtained without any creative efforts.

(a) A burn-infliction device. (b) A burn wound formed. (c) Histological analysis of the burn wound (×40 magnification) 24 hours after burn injury. (d) This figure is a high magnification view of the area indicated in 1c. (e) An eschar formed at 3 weeks after burn injury. (f) Clearance of necrotic eschar at 3 weeks after burn injury and creation of porcine full-thickness burn wounds. (g) This invention. (h) The wounded porcine covered with homemade elasticated jackets. Scale bar=200 µm.

FIG. 8. Quantification of P63 staining. Significance of the differences between this invention and saline was set at *p<0.05. Significance of the differences between rhEGF and saline was set at #p<0.05. Significance of the differences between this invention and rhEGF was set at ±p<0.05. Error bars indicate SEM.

FIG. 9. Quantification of CK10 staining. Significance of the differences between rhEGF and saline was set at #p<0.05. Significance of the differences between this invention and rhEGF was set at ±p<0.05. Error bars indicate SEM.

DETAILED DESCRIPTION OF THE INVENTION

The invention is further described with reference to the following drawings and embodiments, so that the objectives, the technical solutions, and the advantages of the present invention are understood more clearly. It is obvious that the embodiments as described are only some embodiments, rather than all embodiments of the present invention. Based on the embodiments of the present invention, all other embodiments obtained by those skilled in the art without creative effort shall fall within the protection scope of the present invention.

The first aspect of the application provides a composition for treating a burn wound, including the following ingredients in mass content: a fatty acid 261-639 mg, an organic substance 3.5-350 mg, a carbohydrate 0.02-60 mg, a vitamin 9-13 µg, a microelement 3.04-5.5 mg, an antibiotic 0.6-70 mg, and an amino acid 105-335 mg.

It should be noted that, in the composition of the first aspect of the present application, the mass content of each ingredient is based on the mass of 1 g composition. Similarly, in the following preferred embodiments, the mass content of each ingredient is also based on the mass of 1 g composition.

Preferably, the specific ingredients of the fatty acid are as follows:

palmitic acid 20-50 mg, stearic acid 10-30 mg, oleic acid 100-200 mg, linoleic acid 100-300 mg, linoleic acid 30-50 mg, butyric acid 0.1-1 mg, hexanoic acid 0.1-1 mg, octanoic acid 0.1-1 mg, myristic acid 0.1-1 mg, palmitoleic acid 0.1-1 mg, heptadecanoic acid 0.1-1 mg, eicosanoic acid 0.1-1 mg, and cis-11-eicosaenoic acid 0.3-2 mg.

Preferably, the specific ingredients of the organic substance are as follows:

ellagic acid 0.1-10 mg, hypaphorine 0.1-10 mg, huperzine C 0.1-10 mg, huperzine A 0.1-10 mg, harmalol 0.1-10 mg, abrine 0.1-10 mg, berberine hydrochloride 0.1-10 mg, 10-gingerol 0.1-10 mg, methyl gallate 0.1-10 mg, spathulenol 0.1-10 mg, 3-furylmethyl 1H-pyrrole-2-carboxylate 0.1-10 mg, tanshinone 0.1-10 mg, dihydrocapsaicin 0.1-10 mg, potassium 7-hydroxy-1-naphthalenesulfonate 0.1-10 mg, pilocarpine 0.1-10 mg, adenosine 0.1-10 mg, firmanoic acid 0.1-10 mg, glabrolide 0.1-10 mg, liquidambaric lactone 0.1-10 mg, schisanlactone 0.1-10 mg, dehydroepiandrosterone 0.1-10 mg, 11(13) dehydroivaxillin 0.1-10 mg, 2-hydroxy evanolactone 0.1-10 mg, 14,15beta-dihydroxyklaineanone 0.1-10 mg, olaquindox 0.1-10 mg, oridonin 0.1-10 mg, phorbol 0.1-10 mg, harmine 0.1-10 mg, maltol 0.1-10 mg, hypoconitine 0.1-10 mg, 2-O-rhamnosylicariside II 0.1-10 mg, theobromine 0.1-10 mg, theophylline 0.1-10 mg, hordeine 0.1-10 mg, and ephedrine 0.1-10 mg.

Preferably, the specific ingredients of the carbohydrate are as follows:

glucose 0.01-30 mg and fructose 0.01-30 mg.

Preferably, the specific ingredients of the vitamin are as follows:

α-tocopherol 1.5-2.5 µg, β-tocopherol 0.5-1.5 µg, γ-tocopherol 4.5-5.5 µg, tocopherol 2.5-3.5 µg.

Preferably, the specific ingredients of the microelement are as follows:

calcium 0.5-1 mg, iron 0.01-0.1 mg, zinc 0.02-0.2 mg, copper 0.01-0.2 mg, and phosphorus 2.5-4 mg, wherein, calcium, iron, zinc, and copper are added to the composition in the form of soluble salts, such as calcium gluconate, calcium hydrogen phosphate, calcium lactate, calcium chloride, $FeCl_2 \cdot 4H_2O$, ferrous sulfate, ferrous gluconate, zinc gluconate, zinc sulfate, zinc acetate, copper sulfate, copper gluconate, and the like, in which the phosphorus can be added in the form of phosphate, such as sodium phosphate, disodium hydrogen phosphate, potassium dihydrogen phosphate, etc., which are not limited in this application.

Preferably, the specific ingredients of the antibiotic are as follows:

mupirocin 0.1-20 mg, neomycin 0.1-10 mg, polymyxin B 0.1-10 mg, gentamicin 0.1-10 mg, amphotericin B 0.1-10 mg, and vancomycin 0.1-10 mg.

Preferably, the specific ingredients of the amino acid are as follows:

glutamic acid 20-50 mg, arginine 20-40 mg, aspartic acid 10-30 mg, serine 5-20 mg, glycine 5-20 mg, alanine 5-20 mg, tyrosine 5-20 mg, histidine 1-10 mg, proline 1-10 mg, cysteine 1-10 mg, valine 5-10 mg, isoleucine 5-10 mg, leucine 10-30 mg, phenylalanine 5-20 mg, methionine 1-5 mg, threonine 2-15 mg, and lysine 4-15 mg.

The second aspect of the application provides a composition for treating a burn wound, which is recorded in parts by weight and includes the following ingredients: 261-639 parts of a fatty acid, 3.5-350 parts of an organic substance, 0.02-60 parts of a carbohydrate, 0.009-0.013 parts of vitamins E, 3.04-5.5 parts of a microelement, 0.6-70 parts of an antibiotic, and 105-335 parts of an amino acid;

wherein, the fatty acid is at least one selected from the group consisting of oleic acid, linoleic acid, linolenic acid and palmitic acid;

the organic substance is at least one selected from the group consisting of ellagic acid, hypaphorine, huperzine C, huperzine A, harmalol, abrine, berberine hydrochloride, 10-gingerol, methyl gallate, spathulenol, 3-furylmethyl 1H-pyrrole-2-carboxylate, tanshinone, dihydrocapsaicin, potassium 7-hydroxy-1-naphthalenesulfonate, pilocarpine, adenosine, firmanoic acid, glabrolide, liquidambaric lactone, schisandrolactone, dehydroepiandrosterone, 11(13) dehydroivaxillin, 2-hydroxyeupatolide, 14,15beta-dihydroxyklaineanone, olaquindox, oridonin, phorbol, harmine, maltol, hypoaconitine, 2-O-rhamnosylicariside II, theobromine, theophylline, hordeine and ephedrine;

the carbohydrate is at least one selected from the group consisting of fructose and glucose;

the microelement is at least one selected from the group consisting of calcium, iron, zinc, copper, and phosphorus;

the antibiotic is at least one selected from the group consisting of mupirocin, neomycin, polymyxin B, gentamicin, amphotericin B and vancomycin; and the amino acid is at least one selected from the group consisting of glutamic acid, arginine, aspartic acid, serine, glycine, alanine, tyrosine, histidine, proline, cysteine, valine, isoleucine, leucine, phenylalanine, methionine, threonine, and lysine.

The inventors discovered in research that an excellent effect on treating burn wounds is achieved by mixing various substances of specific contents in the composition of the present application. Not limited to any theory, the inventor believes that this may be due to the synergistic effect of the various ingredients.

In this application, the forms of calcium, iron, zinc, copper and phosphorus in the microelement are not limited, as long as they can achieve the purpose of the present invention, wherein calcium, iron, zinc and copper are added in the form of soluble salts, such as calcium gluconate, calcium hydrogen phosphate, calcium lactate, calcium chloride, $FeCl_2 \cdot 4H_2O$, ferrous sulfate, ferrous gluconate, zinc gluconate, zinc sulfate, zinc acetate, copper sulfate, copper gluconate, and the like, in which the phosphorus can be added in the form of a phosphate, such as sodium phosphate, disodium hydrogen phosphate, potassium dihydrogen phosphate, etc., which is not limited in this application.

In this application, vitamin E includes a variety of different natural forms. This application does not limit the specific form of vitamin E as long as the purpose of the present invention can be achieved. For example, vitamin E can be at least one selected from the group consisting of α-tocopherol, β-tocopherol, γ-tocopherol and δ-tocopherol.

Each ingredient in the composition of this application can be purchased from commercial sources.

In some embodiments of the second aspect of the application, the fatty acid also includes at least one selected from the group consisting of stearic acid, butyric acid, hexanoic acid, octanoic acid, myristic acid, palmitoleic acid, heptadecanoic acid, eicosanoic acid, and cis-11-eicosenoic acid; wherein, in parts by weight, the total content of oleic acid, linoleic acid, linolenic acid and palmitic acid is not less than 250 parts.

In some embodiments of the second aspect of the present application, in parts by weight, the fatty acid includes: 20-50 parts of palmitic acid, 10-30 parts of stearic acid, 100-200 parts of oleic acid, 100-300 parts of linoleic acid, 30-50 parts of linolenic acid, 0.1-1 parts of butyric acid, 0.1-1 parts of hexanoic acid, 0.1-1 parts of octanoic acid, 0.1-1s parts of myristic acid, 0.1-1 parts of palmitoleic acid, 0.1-1 parts of heptadecanoic acid, 0.1-1 parts of eicosanoic acid, and 0.3-2 parts of cis-11-eicosaenoic acid.

In some embodiments of the second aspect of the present application, in parts by weight, the organic substance includes: 0.1-10 parts of ellagic acid, 0.1-10 parts of hypaphorine, 0.1-10 parts of huperzine C, 0.1-10 parts of huperzine A 0.1-10 parts of harmalol, 0.1-10 parts of abrine, 0.1-10 parts of berberine hydrochloride, 0.1-10 parts of 10-gingerol, 0.1-10 parts of methyl gallate, 0.1-10 parts of spathulenol, 0.1-10 parts of 3-furylmethyl 1H-pyrrole-2-carboxylate, 0.1-10 parts of tanshinone, 0.1-10 parts of dihydrocapsaicin, 0.1-10 parts of potassium 7-hydroxy-1-naphthalenesulfonate, 0.1-10 parts of pilocarpine, 0.1-10 parts of adenosine, 0.1-10 parts of firmanoic acid, 0.1-10 parts of glabrolide, 0.1-10 parts of liquidambaric lactone, 0.1-10 parts of schisanlactone, 0.1-10 parts of dehydroepiandrosterone, 0.1-10 parts of 11(13)-dehydroivaxillin, 0.1-10 parts of 2-hydroxyeupatolide, 0.1-10 parts of 14,15beta-dihydroxyklaineanone, 0.1-10 parts of olaquindox, 0.1-10 parts of oridonin, 0.1-10 parts of phorbol, 0.1-10 parts of harmine, 0.1-10 parts of maltol, 0.1-10 parts of hypoaconitine, 0.1-10 parts of 2-O-rhamnosylicariside II, 0.1-10 parts of theobromine, 0.1-10 parts of theophylline, 0.1-10 parts of hordeine, and 0.1-10 parts of ephedrine.

In some embodiments of the second aspect of the present application, in parts by weight, the carbohydrate includes 0.01-30 parts of glucose and 0.01-30 parts of fructose.

In some embodiments of the second aspect of the present application, in parts by weight, the vitamin includes 0.0015-0.0025 parts of α-tocopherol, 0.0005-0.0015 parts of β-tocopherol, 0.0045-0.0055 parts of γ-tocopherol, and 0.0025-0.0035 parts of δ-tocopherol.

In some embodiments of the second aspect of the present application, in parts by weight, the microelement includes: 0.5-1 parts of calcium, 0.01-0.1 parts of iron, 0.02-0.2 parts of zinc, 0.01-0.2 parts of copper, and 2.5-4 parts of phosphorus.

In some embodiments of the second aspect of the present application, in parts by weight, the antibiotic includes: 0.1-20 parts of mupirocin, 0.1-10 parts of neomycin, 0.1-10 parts of polymyxin B, 0.1-10 parts of macromycin, 0.1-10 parts of amphotericin B, and 0.1-10 parts of vancomycin.

In some embodiments of the second aspect of the present application, in parts by weight, the amino acid includes: 20-50 parts of glutamic acid, 20-40 parts of arginine, 10-30 parts of aspartic acid, 5-20 parts of serine, 5-20 parts of glycine, 5-20 parts of alanine, 5-20 parts of tyrosine, 1-10 parts of histidine, 1-10 parts of proline, 1-10 parts of cysteine, 5-10 parts of valine, 5-10 parts of isoleucine, 10-30 parts of leucine, 5-20 parts of phenylalanine, 1-5 parts of methionine, 2-15 parts of threonine, and 4-15 parts of lysine.

As for the compound in the present application, each type of ingredient can be separately mixed first, and then the mixed ingredients can be subjected to a second mix. For example, first mix the various ingredients of the fatty acid, mix the various ingredients of the organic substances, mix the various ingredients of the carbohydrate, mix the various ingredients of the vitamin, mix the various ingredients of the microelement, mix the various ingredients of the antibiotic, mix the various ingredients of amino acids, and then introduce these mixed ingredients into one container for a second mix. There is no chemical reaction between the ingredients once the composition is prepared, which only includes a physical mixing. Therefore, the preparation method can be obtained by referring to the physical mixing methods in the prior art, which is not limited in this application.

The present application will be specifically explained based on Examples as follows, although not limited thereto.

Example 1

Mix the following ingredients to obtain the composition of this application:

Linoleic acid 2700 mg, ellagic acid 50 mg, pilocarpine 50 mg, methyl gallate 50 mg, glucose 5 mg, vitamin E 100 μg, calcium lactate 218 mg, mupirocin 100 mg, glutamic acid 500 mg, arginine 400 mg, and tyrosine 200 mg.

Example 2

Mix the following ingredients to obtain the composition of this application:

Oleic acid 2000 mg, linoleic acid 2000 mg, hypaphorine 50 mg, liquidambaric lactone 50 mg, oridonin 50 mg, maltol 50 mg, glucose 100 mg, fructose 100 mg, vitamin E 200 μg, calcium lactate 109 mg, potassium dihydrogen phosphate 136 mg, vancomycin 100 mg, neomycin 100 mg, serine 500 mg, aspartic acid 400 mg, methionine 200 mg, and alanine 400 mg.

Example 3

Mix the following ingredients to obtain the composition of this application:

Palmitic acid 340 mg, stearic acid 130 mg, oleic acid 1080 mg, linoleic acid 2410 mg, linolenic acid 360 mg, butyric acid 1.3 mg, hexanoic acid 5 mg, octanoic acid 5 mg, myristic acid 9 mg, palmitoleic acid 3 mg, heptadecanoic acid 2 mg, eicosanoic acid 4 mg, cis-11-eicosaenoic acid 12 mg, each of ellagic acid, hypaphorine, huperzine C, huperzine A, harmalol, abrine, berberine hydrochloride, 10-Gingerol, methyl gallate, spathulenol, 3-furylmethyl 1H-pyrrole-2-carboxylate, tanshinone, dihydrocapsaicin, potassium 7-Hydroxy-1-naphthalenesulfonate, pilocarpine, adenosine, firmanoic acid, glabrolide, liquidambaric lactone, schisanlactone, dehydroepiandrosterone, 11(13)-dehydroivaxillin, 2-hydroxy edenoid, 14,15beta-dihydroxyklaineanone, olaquindox, oridonin, phorbol, harmine, maltol, hypoaconitine, 2-O-Rhamnosylicariside II, theobromine, theophylline, hordeine, and ephedrine 2 mg, glucose 5 mg, fructose 5 mg, α-tocopherol 18 μg, β-tocopherol 8 μg, γ-tocopherol 55 μg, δ-tocopherol 35 μg, calcium lactate 27 mg, ferrous gluconate 2.6 mg, zinc gluconate 3.4 mg, copper gluconate 0.7 mg, disodium phosphate 128 mg, mupirocin 2 mg, neomycin 100 mg, polymyxin B Sing, gentamicin Sing, amphotericin B Sing, vancomycin Sing, glutamic acid 400 mg, arginine 280 mg, aspartic acid 150 mg, serine 100 mg, glycine 100 mg, alanine 90 mg, tyrosine 60 mg, histidine 40 mg, proline 60 mg, cysteine 20 mg, valine 80 mg, isoleucine 70 mg, leucine 130 mg, phenylalanine 90 mg, methionine 20 mg, threonine 65 mg, and lysine 50 mg.

The sources of the ingredients in each of the above examples are listed in Table 1.

TABLE 1

| | Ingredient | CAS No. | Manufacturer | SPEC | Product ID |
|---|---|---|---|---|---|
| Fatty acids | Palmitic acid | 57-10-3 | Anpel | 5 g | CFEQ-4-510012-0005 |
| | Stearic acid | 57-11-4 | Anpel | 5 g | CFEQ-4-530173-0005 |

TABLE 1-continued

| | Ingredient | CAS No. | Manufacturer | SPEC | Product ID |
|---|---|---|---|---|---|
| | Oleic acid | 112-80-1 | Anpel | 100 mg | CFEQ-4-531190-0001 |
| | Linoleic acid | 60-33-3 | Anpel | 1 g | CFEQ-4-533134-0001 |
| | Linolenic acid | 463-40-1 | Anpel | 5 ml | CFEQ-4-533060-0005 |
| | Butyric acid | 107-92-6 | Anpel | 5 ml | CFEQ-4-420764-0005 |
| | Hexanoic acid | 142-62-1 | Anpel | 100 ml | CFEQ-4-470115-0100 |
| | Octanoic acid | 124-07-2 | Anpel | 5 ml | CFEQ-4-531037-0005 |
| | Myristic acid | 544-63-8 | Anpel | 5 g | CFEQ-4-490486-0005 |
| | Palmitoleic acid | 373-49-9 | Anpel | 100 mg | CFAD-P9417-100 MG |
| | Heptadecanoic acid | 506-12-7 | Anpel | 25 g | CFLD-H122278-25 g |
| | Eicosanoic acid | 506-30-9 | Anpel | 100 mg | CDFT-016-05721 |
| | cis-11-Eicosenoic acid | 5561-99-9 | Anpel | / | CFAD-E3635-100 MG |
| Organic substances | Ellagic acid | 476-66-4 | Anpel | 20 mg | CDAA-280576-20 mg |
| | Hypaphorine | 487-58-1 | Anpel | 5 mg | CDHJ-ST17000105 MG |
| | Huperzine A | 102518-79-6 | Anpel | 20 mg | CDAA-280495-20 mg |
| | Huperzine C | 163089-71-2 | Chemfaces | 20 mg | CFN90345 |
| | Harmalol | 525-57-5 | Anpel | 1 mg | CDFX-PHY89701 |
| | Abrine | 21339-55-9 | Anpel | 50 mg | CDFV-ALX-106-040-M050 |
| | Berberine hydrochloride | 633-65-8 | Anpel | 20 mg | CDAA-280255-20 mg |
| | 10-Gingerol | 23513-15-7 | Anpel | 20 mg | CDAA-281614-20 mg |
| | Methyl gallate | 99-24-1 | Anpel | 20 mg | CDAA-280761-20 mg |
| | Spathulenol | 6750-60-3 | Anpel | 5 mg | CDBO-B30013-5 mg |
| | 3-furylmethyl 1H-pyrrole-2-carboxylate | 119767-00-9 | Anpel | 5 mg | CDHJ-ST82780105 MG |
| | Tanshinone | 568-73-0 | Anpel | 20 mg | CDAA-281232-20 mg |
| | Dihydrocapsaicin | 19408-84-5 | Anpel | 20 mg | CDBD-CCPE900179 |
| | Potassium 7-Hydroxy-1-naphthalenesulfonate | 30252-40-5 | Anpel | 20 mg | CDAA-281330-20 mg |
| | Pilocarpine | 92-13-7 | Aladdin | 300 mg | 1538505-300 MG |
| | Adenosine | 58-61-7 | Anpel | 100 g | CFLD-A108808-100 g |
| | Firmanoic acid | 107584-83-8 | Chengdu Biopurify Phytochemicals Co., Ltd. | 5 g | MOL-PMIOX-849813 |
| | Glabrolide | 10401-33-9 | Anpel | 5 mg | CDHJ-ST55140105 MG |
| | Liquidambaric lactone | 185051-75-6 | Anpel | 5 mg | CDHJ-ST16000105 MG |
| | Schisanlactone | 136040-43-2 | Baoji Earay Bio-Tech Co., Ltd | 10 mg | YRS1574 |
| | Dehydroepiandrosterone (DHEA) | 53-43-0 | Anpel | 20 mg | CDBO-DT0053 |
| | 11(13)-Dehydroivaxillin | 87441-73-4 | Shanghai Yuanmu Biological Technology Co., Ltd. | / | YM-0019 |
| | 2-hydroxyeupatolide | 72229-33-5 | Anpel | 10 mg | CDHI-E-0192 |
| | 14,15beta-Dihydroxyklaineanone | 137359-82-1 | Anpel | 20 mg | CDHJ-ST82530105 MG |
| | Olaquindox | 23696-28-8 | Anpel | 100 mg | CDBD-CCAD300339 |
| | Oridonin | 28957-04-2 | Anpel | 50 mg | CFLD-O111382-50 mg |
| | Phorbol | 17673-25-5 | Anpel | 20 mg | CDHJ-ST24390120 MG |
| | Harmine | 442-51-3 | Anpel | 1 g | CDFT-3 51-00361 |
| | Maltol | 118-71-8 | Anpel | 100 mg | CDBD-CCPD101352 |
| | Hypaconine | 63238-68-6 | Chengdu Biopurify Phytochemicals Co., Ltd. | 5 mg | BP3199-5 mg |
| | 2-O-Rhamnosylicariside II | 135293-13-9 | Anpel | 5 mg | CDHJ-ST18550105 MG |
| | Theobromine | 83-67-0 | Anpel | 20 mg | CDAA-280904-20 mg |
| | Theophylline | 58-55-9 | Anpel | 5 g | CFEQ-4-401712-0005 |
| | Hordenine | 539-15-1 | Anpel | 20 mg | CDAA-281238-20 mg |
| | Ephedrine | 299-42-3 | Anpel | 25 g | CFGF-158940250 |
| Carbohydrates | Glucose | 50-99-7 | Anpel | 100 g | CFEQ-4-532058-0005 |
| | D-Fructose | 57-48-7 | Anpel | 5 g | CFEQ-4-460070-0005 |
| Vitamins | α-Tocopherol | 10191-41-0 | Anpel | 5 g | CFAE-258024-5 G |
| | β-Tocopherol | 16698-35-4 | Anpel | 25 mg | CDDM-T526130-25 mg |
| | γ-Tocopherol | 54-28-4 | Anpel | 25 mg | CFAD-T1782-25MG |
| | δ-Tocopherol | 119-13-1 | Anpel | 100 mg | CDAA-120001-100 MG |
| Microelements | Calcium | 814-80-2 | Anpel | 50 g | CFBO-2009 |
| | Iron | 299-29-6 | Anpel | 500 g | CDFT-096-00785 |
| | Zinc | 4468-02-4 | Anpel | 5 g | CFEQ-4-540015-0005 |
| | Copper | 527-09-3 | Anpel | 100 g | CFEQ-4-441860-0100 |
| | Phosphorus | 7558-79-4 | Anpel | 50 mg | CDCT-C13000000 |
| Antibiotics | Mupirocin | 12650-69-0 | Anpel | 100 mg | CDGO-130568 |
| | Neomycin | 1405-10-3 | Anpel | 200 mg | CDGO-130309 |
| | Polymyxin B | 1404-26-8 | Anpel | 2.25 mg | CMLQ-P-36H |
| | Gentamycin | 1403-66-3 | Anpel | 0.1 g | CMLQ-P-04 |
| | Amphotericin B | 1397-89-3 | Anpel | 250 mg | CDFT-015-13361 |
| | Vancomycin | 1404-93-9 | Anpel | 0.2 g | CMLQ-P08 |
| Amino acids | Glutamic acid | 56-86-0 | Anpel | 200 mg | CDAA-270005-200 mg |
| | Arginine | 74-79-3 | Anpel | 200 mg | CDAA-270002-200 mg |
| | Aspartic acid | 56-84-8 | Anpel | 200 mg | CDAA-270003-200 mg |
| | Serine | 56-45-1 | Anpel | 200 mg | CDAA-270014-200 mg |
| | Glycine | 56-40-6 | Anpel | 100 g | CFEQ-4-532109-0100 |

TABLE 1-continued

| Ingredient | CAS No. | Manufacturer | SPEC | Product ID |
|---|---|---|---|---|
| Alanine | 56-41-7 | Anpel | 200 mg | CDAA-270018-200 mg |
| Tyrosine | 60-18-4 | Anpel | 200 mg | CDAA-270016-200 mg |
| Histidine | 71-00-1 | Anpel | 200 mg | CDAA-270007-200 mg |
| Proline | 147-85-3 | Anpel | 200 mg | CDAA-270013-200 mg |
| Cysteine | 52-90-4 | Anpel | 200 mg | CDAA-270022-200 mg |
| Valine | 72-18-4 | Anpel | 200 mg | CDAA-270017-200 mg |
| Isoleucine | 73-32-5 | Anpel | 200 mg | CDAA-270008-200 mg |
| Leucine | 61-90-5 | Anpel | 200 mg | CDAA-270009-200 mg |
| Phenylalanine | 63-91-2 | Anpel | 200 mg | CDAA-270012-200 mg |
| Methionine | 63-68-3 | Anpel | 100 g | CFLD-M101130-100 g |
| Threonine | 72-19-5 | Anpel | 200 mg | CDAA-270015-200 mg |
| Lysine | 56-87-1 | Anpel | 200 mg | CDAA-270010-200 mg |

Test Example 1: Animal Full-Thickness Burn Healing Experiment (1) Animal Ethics: The Ethical Approval of this experiment has been acquired. Animals used in the experiment were treated humanely. The experiment process complies with the relevant regulations of Animal Health and Protection Act and the Code of Practice for Animal Care and Use for Scientific Purposes.

(2) Experimental animals: Three female Guangxi Bama mini-pigs are 19-21 kilograms (provided by Tianjin Bainong Laboratory Animal Breeding Technology Co., Ltd., Tianjin, China). Animals were housed in isolated steel cages (80× 100×110 $cm^3$) at 25° C. under natural lighting in the Experimental Animal Center, after thoroughly disinfecting the breeding room and the cages for animals with disinfectants and ultraviolet lamps. Non-experimental personnel are strictly prohibited from entering the breeding room during the experiment Animals were fed with standard pig chow twice daily, 150 grains at a time, and had access to water ad libitum (water is of the clean standard for tap water). The breeding room and cage are disinfected regularly on a weekly basis, and the feed tank and the water sink are cleaned before each feeding.

(3) Creation of porcine full-thickness burn wound models: The miniature pig was raised conventionally, fasted for 12 h, laid on one side, and injected with sumianxin injection into the hip muscle. Once anesthetized, the miniature pig was transferred to an operating table and a ventilation tube was placed in the mouth. After disinfection of the back of the ear, an indwelling needle of the auricle vein was placed for adequate analgesia and sedation. The surgical area on the back was prepared, disinfected with iodophor, on which a sterile sheet was spread, and an expected site of a burn was marked. The aluminum block mold (the net weight of the aluminum block mold is 265 g, and the load is 1 kg) was heated to 96° C. for 10 minutes, and was in close contact with the skin for 45 seconds. Each pig had 9 wounds. The operation on the back of the 3 mini pigs is consistent. After the operation, the wounds were disinfected with iodophor, on which cotton pads dressing and elastic sleeves were applied. Antibiotics were injected intravenously to prevent infection, and 2 ml of the awakening agent Lu Xingning was injected intravenously. The pigs were then transferred to the cages. One hour after waking up, the pigs were fed and given oral rehydration saline. Activities and signs of the pigs were closely observed. After the burn injury, local debridement and different treatments were performed on the wounds. Three weeks after injury, the wounds were covered by necrotic eschar, without exudate and dissolution reaction. Excisional debridement down to the fat layer was performed. Wounds were then dressed and covered with elasticated jackets to prevent animal-initiated damage. Preemptive antibiotics and analeptic Lu Xingning were administered i.v., then the animals were transferred to individual cages, and monitored closely for adverse outcomes during their post-procedure recovery. Post-surgical pain was managed with oral analgesia.

Figure 1:
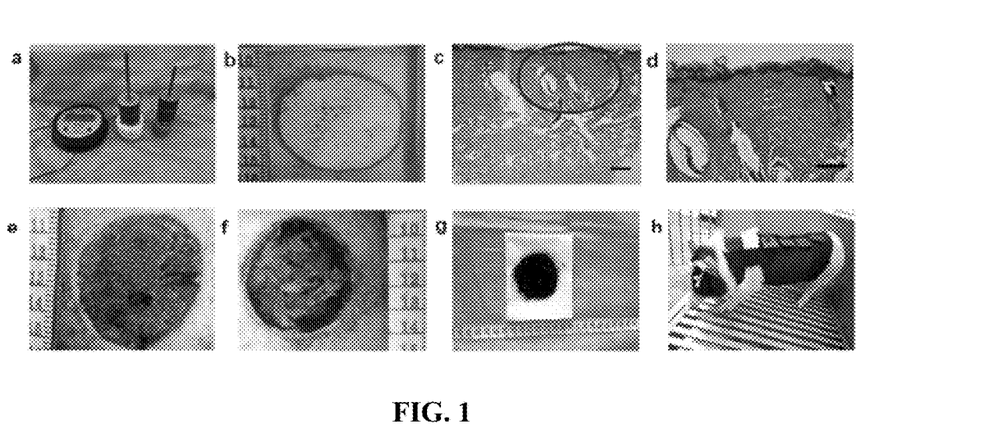
FIG. 1. Creation of porcine full-thickness burn wound models.

FIG. 1. Creation of porcine full-thickness burn wound models. (a) The burn-infliction device for heating aluminium block mold. (b) A burn wound formed. (c) Histological analysis of the burn wound (×40 magnification) 24 hours after burn injury, scale bar=200 μm. (d) This figure is a high magnification view of the area indicated in (c), scale bar=200 μm. (e) The eschar formation at 3 weeks after burn injury. (f) Clearance of necrotic eschar at 3 weeks after burn injury and creation of porcine full-thickness burn wounds. (g) The appearance of the composition of Example 3 of the present invention. (h) The wounded porcine covered with homemade elasticated jackets.

(4) Wound healing assessment

In order to verify the therapeutic effect of the composition of this application on burn wounds, the composition of Example 3 of this application, recombinant human epidermal growth factor rhEGF (5000 IU/mL, 15 mL, Shenzhen Watsin Genetech Ltd.) and physiological saline were used respectively to treat the full-thickness burn wounds of the pigs.

Figure 2:
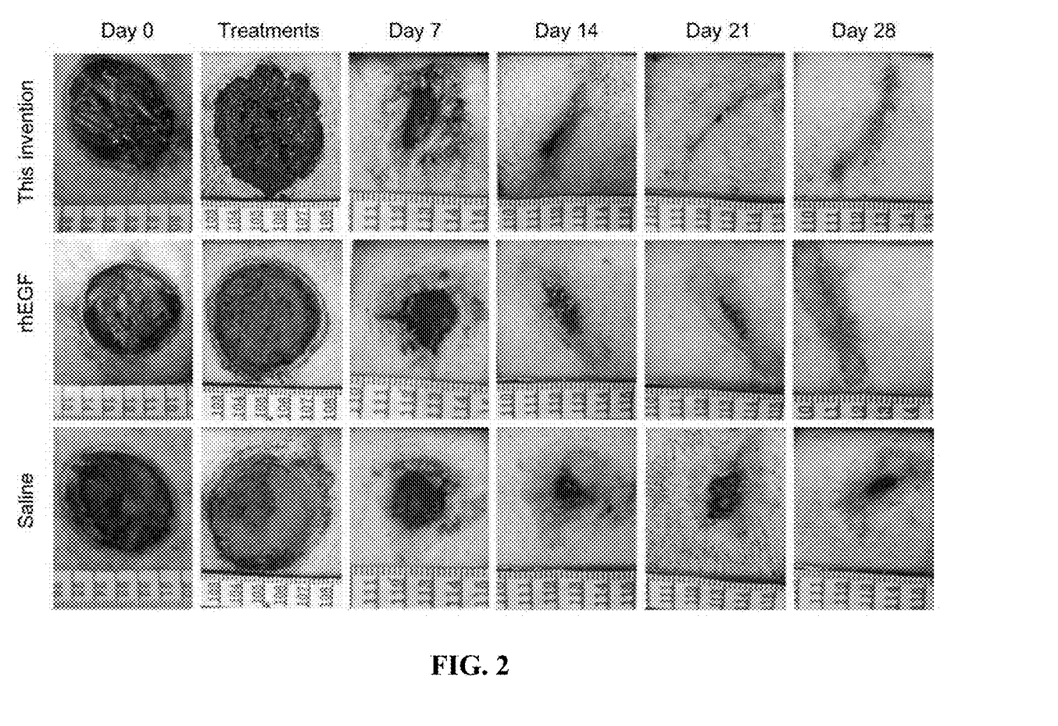
FIG. 2. Effects of this invention on porcine full-thickness burn wounds. Gross appearances of the wounds after treatments with this invention, rhEGF and saline for 1, 2, 3 and 4 weeks.

The wounds were photographed and measured at day 7, 14, 21, 28 after different treatments. The wound healing with time is shown in FIG. 2. It can be seen from FIG. 2 that the new granulation tissue of the wound is fresh and rosy without exudation. The skin in the healing part of the wound forms a scar with darker color and slightly harder texture than normal skin, which is slightly higher than the surrounding normal skin, and the wound healing part has no hair growth. There are no reactions, such as redness, blisters, or ulceration around the wound, and no deterioration, such as further enlargement or necrosis. It can be seen from the local conditions of the wound at day 28 after treatment that the area of scar formed after the treatment with the present invention is smaller and lighter in color than that of the rhEGF group. The wounds in both groups treated with the present invention and the rhEGF heal faster than those of the saline group.

Figure 3:
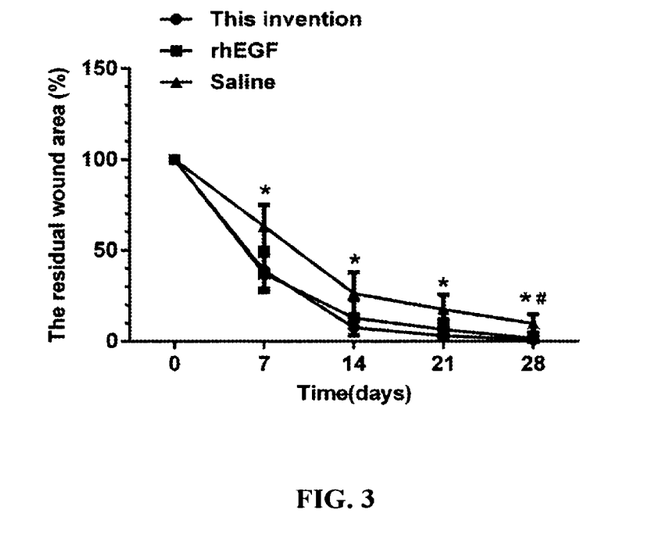
FIG. 3. Quantification of residual wound area (burn wound area after treatment/burn wound area at baseline× 100%) at week 1, 2, 3, and 4 after the treatment. Significance of the differences between this invention and saline was set at *p<0.05. Significance of the differences between rhEGF and saline was set at #p<0.05. Error bars indicate SEM.
Figure 4:
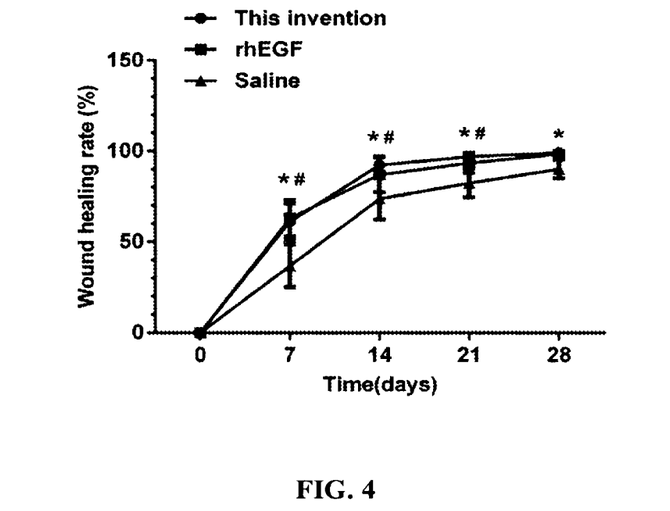
FIG. 4. Quantification of wound healing rate (burn wound area at baseline-burn wound area after treatment/burn wound area at baseline×100%) at week 1, 2, 3, and 4 after the treatment. Significance of the differences between this invention and saline was set at *p<0.05. Significance of the differences between rhEGF and saline was set at #p<0.05. Error bars indicate SEM.

The changes of the residual wound area and the wound healing rate are shown in FIG. 3 and FIG. 4, respectively, wherein the residual wound area (%)=(burn wound area after treatment/burn wound area at baseline) 100%, and the wound healing rate (%)=(burn wound area at baseline−burn wound area after treatment)×100%. It can be seen from FIG. 3 that the present invention obviously reduced wound area at day 7, 14, 21, 28 after treatment, compared to the saline group (*p<0.05, compared with the physiological saline group). The positive control rhEGF obviously reduced wound area at day 28 after treatment, compared to the saline group (#p<0.05, compared with the physiological saline group). These data suggests that the present invention has significantly reduced wound area. FIG. 4 shows that the present invention obviously improved wound healing rate at day 7, 14, 21, 28 after treatment, compared to the saline group (*p<0.05, compared with the physiological saline group). The positive control rhEGF obviously improved the wound healing rate at day 7, 14, 21 after treatment, compared with saline group (#p<0.05, compared with the physiological saline group). There were no significant differences between the present invention and rhEGF (p=0.946). These data suggests that the present invention has improved healing rate of burn wounds.

Figure 5:
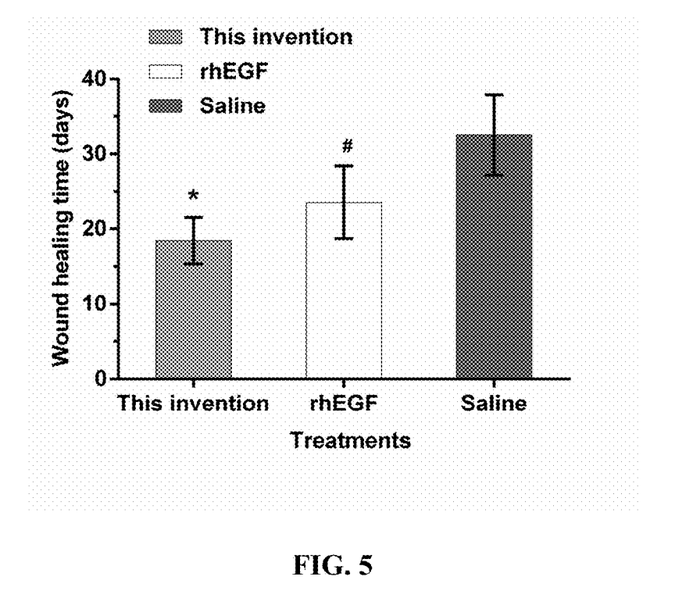
FIG. 5. Quantification of wound healing time at week 1, 2, 3, and 4 after treatment. Significance of the differences between this invention and saline was set at *p<0.05. Significance of the differences between rhEGF and saline was set at #p<0.05. Error bars indicate SEM.

Wound healing time is defined as the time taken to reach complete epithelialization. Individual burn wounds were clinically assessed and photographed at day 7, 14, 21, 28 post-treatment. As shown in Table 2 and FIG. 5, the time required to achieve complete wound healing was 18.44±3.09 days in the present invention, 23.56±4.85 days in the rhEGF group, and 32.56±5.36 days in the saline group (FIG. 5 & Table 2). These data indicated that the present invention significantly shortens the wound healing time. No difference is observed between the wounds treated with the present invention of interest and those treated with rhEGF (p=0.063), indicating that the effect and the wound healing time of the composition of the present application on wounds is equivalent to those of rhEGF. In FIG. 5, * represents the statistical significance of between this invention and the negative control group; # represents the statistical significance between rhEGF and the negative control group.

TABLE 2

Comparison of wound healing time

| Group | Number of cases | Wound healing time (days, $\overline{X}$ +/− S) | F | P |
|---|---|---|---|---|
| This invention | 9 | 18.44 ± 3.09[1,3] | 22.288 | <0.001 |
| rhEGF | 9 | 23.56 ± 4.85[2] | | |
| Saline | 9 | 32.56 ± 5.36 | | |

[1]P < 0.01 This invention versus Saline group.
[2]p < 0.01 rhEGF versus Saline group.
[3]p > 0.05 This invention versus rhEGF.

Wound Healing Assessment (Histologic and Immunohistochemical Analysis)

An immunohistochemistry analysis was performed to identify the localization and expression of specific molecular markers of keratinocytes in the healed epidermis. The results of immunohistochemistry and Masson staining at 4 weeks after treatment on wounds are shown in FIG. 6.

Figure 6:
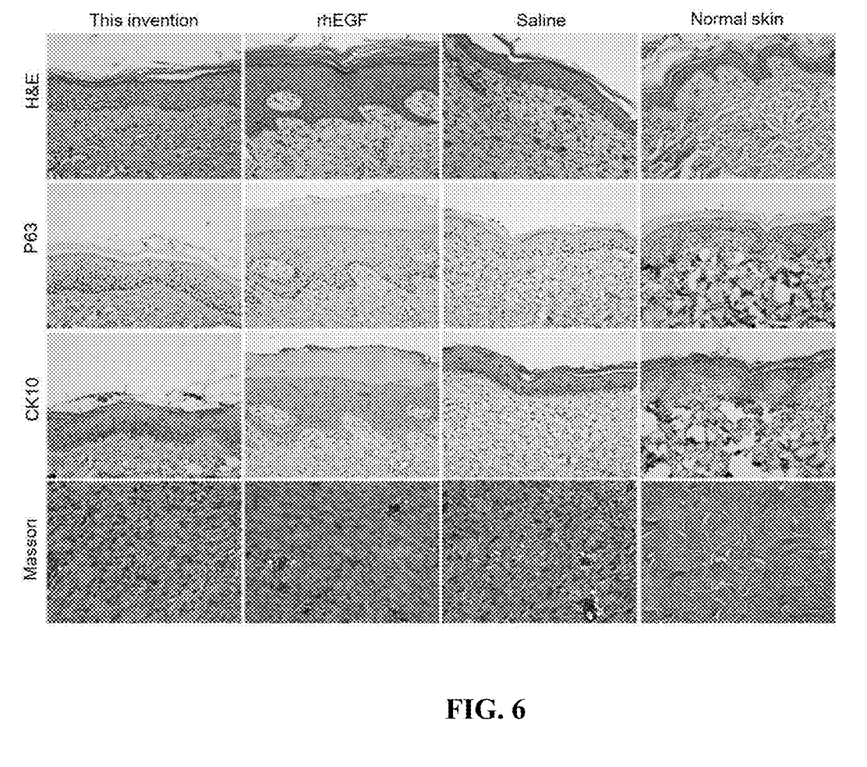
FIG. 6. Histologic and immunohistochemical staining analysis of the treated burn wounds at day 28 after treatment with the composition of the present invention, rhEGF and saline, with immunohistochemical staining of CK10, P63 in newly formed epidermis, and Masson's Trichrome staining in newly formed dermis. Scale bar=100 µm.

It can be seen from FIG. 6 that the nuclear transcription factor P63 was mainly expressed in undifferentiated proliferating keratinocytes located in the basal layer. CK 10 was mainly expressed in mature differentiating keratinocytes. The expression of P63 and CK10 protein indicate the proliferation and differentiation of keratinocytes during epithelialization and repair of wounds. The higher the expression of P63 and CK10 protein, the faster the cells proliferate and differentiate. In the late stage of wound repair, fibroblasts secrete more collagen fibers, and a large number of collagen fibers increase and are densely arranged. Masson staining is used to mark the subcutaneous collagen fibers as green. The structure of each layer of the epidermis treated with the present invention is clear. The proliferative layer and the differentiated layer can be clearly identified by immunohistochemical staining.

Figure 8:
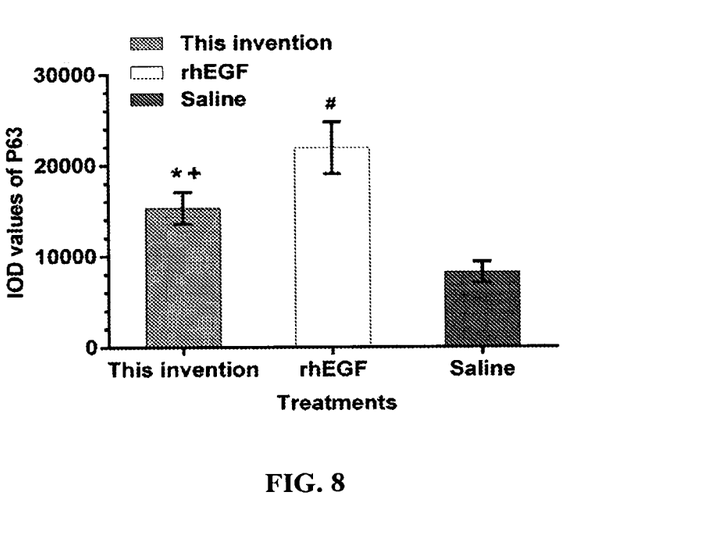
Figure 9:
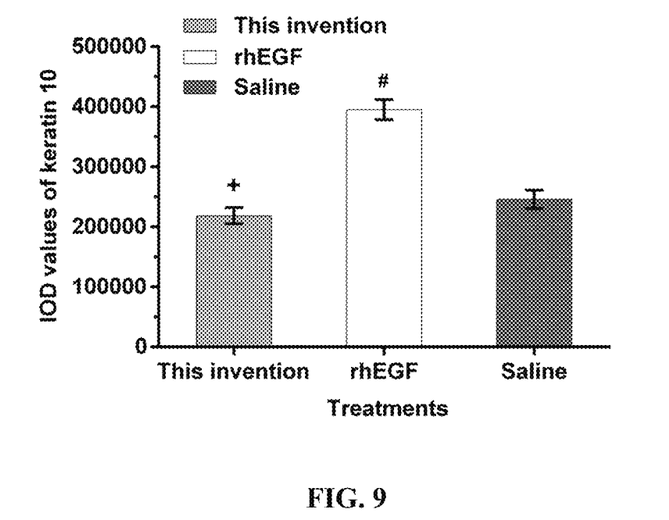

Integrated optical density (IOD) values analysis of immunohistological images of P63 and CK10 are performed by Image-Pro Plus 6.0, as shown in Table 3 and FIGS. 8 to 9. The expression of P63 in the healed epidermis treated with the present invention was significantly weaker than that of the rhEGF group, but stronger than that of the saline group (p<0.05). (In FIG. 8, * represents the statistical significance between this invention and the saline group; # represents the statistical significance between the rhEGF group and the saline group; + represents the statistical significance between this invention and the rhEGF group.) The expression of CK10 protein treated with the present invention was weaker than that of the rhEGF group. (In FIG. 9, * represents the statistical significance between this invention and the saline group; # represents the statistical significance between the rhEGF group and the saline group; + represents the statistical significance between this invention and the rhEGF group.) It should be noted that overexpression of P63 and CK10 protein means cell overproliferation and overdifferentiation, resulting in excessively thick proliferation and differentiation layers in the epidermis, and thus scars are easily formed. The expression of P63 and CK10 protein in the present invention is weaker than that of the rhEGF group, so that the scars after wound healing are less likely to be formed.

TABLE 3

Integrated optical density (IOD) of immunohistochemistry

| Group | IOD (P63) ($\overline{X}$ +/− S) | F | P | IOD (CK10) ($\overline{X}$ +/− S) | F | P |
|---|---|---|---|---|---|---|
| This invention | 15311.09 ± 10443.27[1,3] | 11.292 | <0.05 | 218625.08 ± 81454.75[3] | 39.312 | <0.05 |
| rhEGF | 21929.27 ± 17138.00[2] | | | 395254.15 ± 99751.14[2] | | |
| Saline | 8216.11 ± 6860.73 | | | 245901.76 ± 90848.92 | | |

[1]P < 0.05, This invention versus Saline group;
[2]P < 0.05, rhEGF versus Saline group;
[3]P < 0.05, This invention versus rhEGF.

Figure 7:
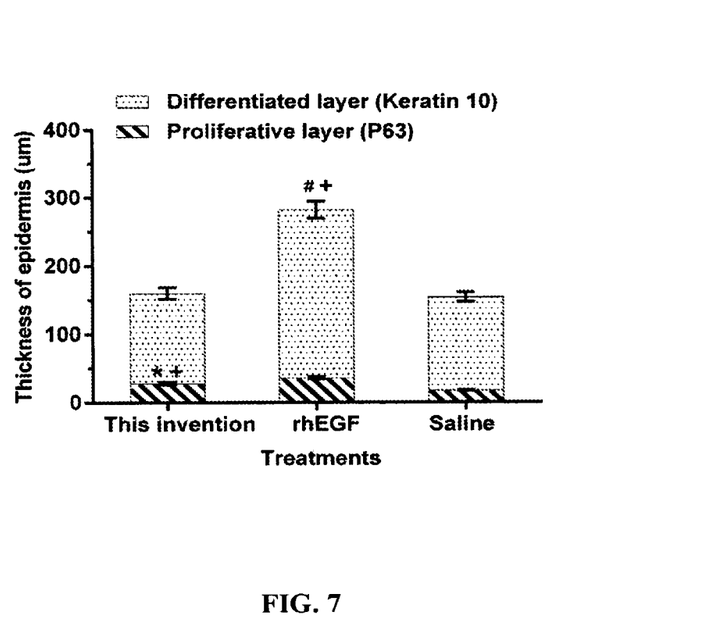
FIG. 7. Quantification of epidermal thickness at week 1, 2, 3, and 4 after treatment (the proliferative and differentiated layers, µm). Significance of the differences between this invention and saline was set at *p<0.05. Significance of the differences between rhEGF and saline was set at #p<0.05. Significance of the differences between this invention and rhEGF was set at +p<0.05. Error bars indicate SEM.

The epidermis partitions into two layers: a proliferative layer and a differentiated layer. The thickness of each of these two layers treated with the present invention was significantly thinner than that of the healed skin tissue treated with rhEGF, as shown in Table 4 and FIG. 7 (* represents the statistical significance between this invention and the saline group; # represents the statistical significance between the rhEGF group and the saline group; + represents the statistical significance between this invention and the rhEGF group). The results indicate that the use of the present invention to treat wounds will produce smaller scars than rhEGF treatment.

TABLE 4

Comparison of the thickness between proliferative layer and differentiated layer

| Group | Thickness of proliferative layer ($\bar{X}$ +/− S) (μm) | F | P | Thickness of differentiated layer ($\bar{X}$ +/− S) (μm) | F | P |
|---|---|---|---|---|---|---|
| This invention | 28.00 ± 10.16[1, 3] | 40.224 | <0.05 | 132.32 ± 50.49[3] | 44.032 | <0.05 |
| rhEGF | 35.92 ± 10.39[2] | | | 246.20 ± 76.47[2] | | |
| Saline | 17.37 ± 4.63 | | | 137.24 ± 42.04 | | |

[1] $P < 0.05$, This invention versus Saline group;
[2] $P < 0.05$, rhEGF versus Saline group;
[3] $P < 0.05$, This invention versus rhEGF.

The above results from porcine study indicate that the present invention has a significant healing effect on wounds, especially non-healing wounds (full-thickness burn wounds). The wound healing rate and healing time of the present invention are equivalent to those of the rhEGF group, indicating that the present invention has a good effect of treating burn wounds. More importantly, compared with the rhEGF group, the epidermal proliferative layer and the differentiated layer treated with the present invention are thinner, which means that the probability of scarring is less. From this perspective, the present invention has a better therapeutic effect than rhEGF. Moreover, the present invention has a lower cost than rhEGF, which is beneficial to clinical application and popularization, and reduces the economic burden of patients.

Test Example 2. Verification of Wound Healing in Patients with Burn Wounds

Clinically, non-healing wounds refer to wounds that do not heal or show no healing tendency after 1 month of treatment. In this application, medical records of 430 patients, including 368 male and 60 female, aged from 1 to 70 years old, with a clinical diagnosis of at least one non-healing burn wound were collected. The burn injury includes 150 cases of hydrothermal burns, 167 cases of flame burns, 84 cases of electric burns, and 29 cases of chemical burns. The 430 patients had an area of a third-degree burn of 0.2%-53.5% TBSA (total body surface area), and an area of a non-healing burn wound formed thereafter of 0.1%-7% TBSA. The non-healing wounds of 430 patients were treated with the composition of Example 3 of the present invention (49 cases), surgery (197 cases), and conventional treatment (rhEGF therapy) (184 cases). There were no statistically significant differences observed among the groups in terms of gender, age, and wound area ($p>0.05$) (The comparison results of the differences in terms of various factors are shown in Tables 5, 6 and 7).

TABLE 5

Comparison of gender in different treatment groups

| Group | Gender (male/female) | $X^2$ value | Sig | P |
|---|---|---|---|---|
| This invention | 41/8 | 2.360 | 0.307 | >0.05 |
| Surgery group | 164/33 | | | |
| Conventional treatment | 163/21 | | | |

TABLE 6

Comparison of age in different treatment groups

| Group | Age ($\bar{x} \pm s$) | F value | Sig | P |
|---|---|---|---|---|
| This invention | 31.04 ± 15.49 | 0.111 | 0.895 | >0.05 |
| Surgery group | 29.88 ± 17.07 | | | |
| Conventional treatment | 30.41 ± 16.59 | | | |

TABLE 7

Comparison of burn wound area in different treatment groups

| Group | TBSA | F value | Sig | P |
|---|---|---|---|---|
| This invention | 1.79% ± 0.01 | 2.837 | 0.060 | >0.05 |
| Surgery group | 2.21% ± 0.01 | | | |
| Conventional treatment | 1.87% ± 0.01 | | | |

The wound healing of different groups (total effective rate) is shown in Table 8. Among the 49 patients in the present invention, the wound was completely healed in 31 cases (63.27%), effectively healed in 15 cases (30.61%), improved in 2 cases (4.08%), and not healed in 1 case (2.04%). Among the 197 patients in the surgery group, the wound was completely healed in 152 cases (77.15%), effectively healed in 39 cases (19.80%), improved in 6 cases (3.05%), and not healed in 0 case (0%). Among the 184 patients in the conventional treatment group, the wound was completely healed in 96 cases (52.17%), effectively healed in 56 cases (30.43%), improved in 24 cases (13.05%), and not healed in 8 cases (4.35%). The effect of the present invention on wound healing is analyzed by the total effective rate after receiving different treatments. The total effective rate=(the number of completely healed cases+the number of effectively healed cases)/total number of cases. The total effective rate of the present invention and the surgery group in treating non-healing burn wounds was significantly higher than that of the conventional treatment group, and the difference was statistically significant ($P<0.05$). However, there is no significant difference between the total effective rate of the present invention and that of the surgery group ($P>0.05$), indicating that the therapeutic effect of the present invention on the non-healing wounds of patients is equivalent to that of the surgical group, and is significantly better than that of the conventional treatment group.

TABLE 8

Wound healing assessment (cases/percentage)

| Group | Number of cases | Completely healed case (%) | Effectively healed case (%) | Improved case (%) | Not healed case (%) | Total effective rate (%) | $X^2$ test | P |
|---|---|---|---|---|---|---|---|---|
| This invention | 49 | 31 (63.27%) | 15 (30.61%) | 2 (4.08%) | 1 (2.04%) | 93.88%[1, 3] | 23.445 | <0.05 |

TABLE 8-continued

| | | Wound healing assessment (cases/percentage) | | | | | |
|---|---|---|---|---|---|---|---|
| Group | Number of cases | Completely healed case (%) | Effectively healed case (%) | Improved case (%) | Not healed case (%) | Total effective rate (%) | $X^2$ test   P |
| Surgery group | 197 | 152 (77.15%) | 39 (19.80%) | 6 (3.05%) | 0 (0%) | 96.95%[2] | |
| Conventional treatment | 184 | 96 (52.17%) | 56 (30.43%) | 24 (13.05%) | 8 (4.35%) | 82.61% | |

[1] $P < 0.05$ This invention versus Conventional treatment group;
[2] $P < 0.05$ Surgery group versus Conventional treatment group;
[3] $P > 0.05$ This invention versus Surgery group.

The comparison of wound healing time is shown in Table 9. The wound healing time of the present invention group, surgery group and conventional dressing group is 19.87±9.10 days, 22.71±11.77 days and 36.71±10.60 days, respectively. Compared with the conventional treatment group, the wound healing time of the present invention group and surgery group were significantly shorter than the conventional treatment group (P<0.05). There is no significant difference in wound healing time between the present invention group and the surgery group (P>0.05). It shows that the wound healing time of the present invention is equivalent to that of the surgery group, and is significantly shorter than that of the conventional treatment group.

TABLE 9

| | | Wound healing time (days) | | |
|---|---|---|---|---|
| Group | Number of cases | Wound healing time ($\bar{X}$ +/− S) | F | P |
| This invention | 31 | 19.87 ± 9.10[1,3] | 54.311 | <0.001 |
| Surgery group | 152 | 22.71 ± 11.77[2] | | |
| Conventional treatment | 96 | 36.71 ± 10.60 | | |

[1] $P < 0.05$ This invention versus Conventional treatment group;
[2] $P < 0.05$ Surgery group versus Conventional treatment group;
[3] $P > 0.05$ This invention versus Surgery group.

Figure 10:
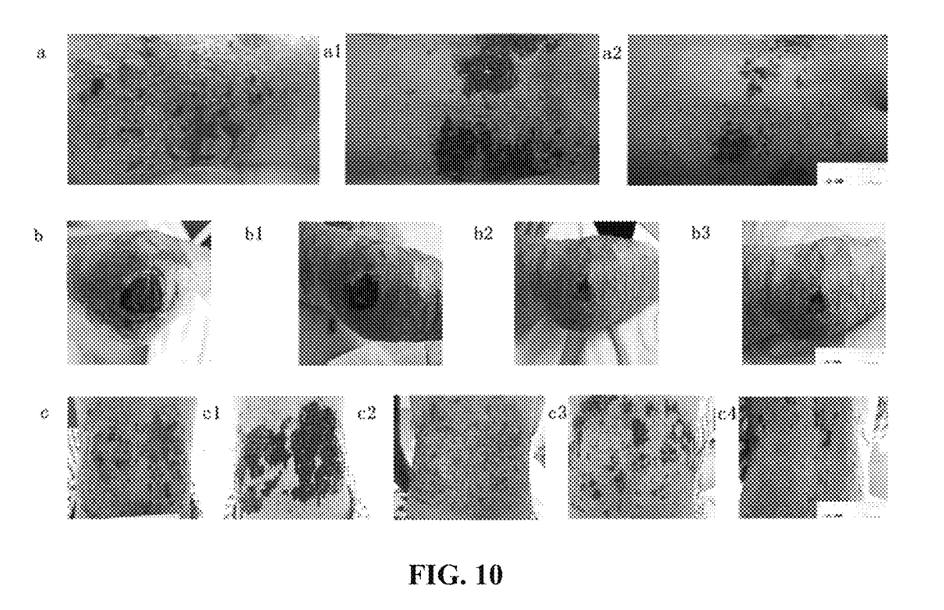
FIG. 10. Effects of this invention on human non-healing burn wounds. (a) Non-healing wounds on the back of a child over 1 month. (a1) This invention applied on wounds. (a2) 4 days after the treatment. (b) A non-healing wound on elbow over 1 month. (b1) This invention applied on the wound. (b2) 1 week after the treatment. (b3) 2 weeks after the treatment. (c) Non-healing wounds on the back of an adult over 1 month. (c1) This invention applied on wounds. (c2) 3 days after the treatment. (c3) 7 days after the treatment. (c4) 10 days after the treatment.

An example of the curative effect of the present invention on human non-healing burn wounds is shown in FIG. 10. (a) Non-healing wounds on the back of a child over 1 month. (a1) This invention applied on wounds. (a2) The wound healing at day 4 after the treatment. (b) A non-healing wound on elbow over 1 month. (b1) This invention applied on wounds. (b2) The wound healing at week 1 after the treatment. (b3) The wound healing at week 2 after the treatment. (c) Non-healing wounds on the back of an adult over 1 month. (c1) This invention applied on wounds. (c2) The wound healing at day 3 after the treatment. (c3) The wound healing at day 7 after the treatment. (c4) The wound healing at day 10 after the treatment.

The above results show that the present invention shows significantly improved effect on wound healing compared with that of clinical conventional treatment.

Test Example 3. Verification of the Therapeutic Effect of the Respective Compositions Prepared in Example 1 and Example 2 of the Present Invention on Porcine Full-Thickness Burn Wounds The porcine full-thickness burn wound models were created with the method described in Example 1. The respective compositions prepared in Example 1 and Example 2 of the present invention were used to treat the wounds. rhEGF was used as a control. The wound healing time is shown in Table 10. It is shown that the present application shortens the wound healing time compared with rhEGF.

TABLE 10

| | | Comparison of wound healing time of the composition prepared in Example 1 and Example 2 | | |
|---|---|---|---|---|
| Group | Number of Cases | Wound healing time (days) ($\bar{X}$ +/− S) | F | P |
| Example 1 | 9 | 19.35 ± 4.21[1,3] | 23.45 | <0.001 |
| Example 2 | 9 | 20.61 ± 2.83[1,3] | 22.98 | |
| rhEGF | 9 | 23.56 ± 4.85[2] | | |
| Saline | 9 | 32.56 ± 5.36 | | |

[1] $P < 0.05$, This invention versus Saline group;
[2] $P < 0.05$, rhEGF versus Saline group;
[3] $P < 0.05$, This invention versus rhEGF.

The descriptions above are only the preferred embodiments of the present invention and are not intended to limit the present invention. Any modification, equivalent replacement, improvement, etc. made within the spirit and principle of the present invention shall be included in the protection scope of the present invention.

The invention claimed is:

1. A composition for treating a burn wound, wherein the composition comprises the following ingredients in parts by weight: 261-639 parts of a fatty acid, 3.5-350 parts of an organic substance, 0.02-60 parts of a carbohydrate, 0.009-0.013 parts of vitamin E, 3.04-5.5 parts of a microelement, 0.6-70 parts of an antibiotic, and 105-335 parts of an amino acid; wherein,
   the fatty acid comprises linoleic acid, and optionally comprises an additional fatty acid selected from the group consisting of oleic acid, palmitic acid, linolenic acid, and a combination thereof;
   the organic substance comprises a first organic substance selected from the group consisting of a first subcombination of ellagic acid, pilocarpine and methyl gallate, a second subcombination of hypaphorine, liquidambaric lactone, oridonin and maltol, and a combination thereof and optionally comprises an additional organic substance selected from the group consisting of huperzine C, huperzine A, harmalol, abrine, berberine hydrochloride, 10-gingerol, spathulenol, 3-furylmethyl 1H-pyrrole-2-carboxylate, tanshinone, dihydrocapsaicin, potassium 7-hydroxy-1-naphthalenesulfonate, pilocarpine, adenosine, firmanoic acid, glabrolide, schisandrolactone, dehydroepiandrosterone, 11,13-dehydroivaxillin, 2-hydroxyeupatolide, 14,15-beta-dihydroxyklaineanone, olaquindox, phorbol, harmine, hypaconine, 2-O-rhamnosylicariside II, theobromine, theophylline, hordenine, ephedrine, and a combination thereof;

the carbohydrate comprises glucose, and optionally comprises fructose;

the microelement comprises calcium, and optionally comprises an additional microelement selected from the group consisting of iron, zinc, copper, phosphorus, and a combination thereof;

the antibiotic comprises a first antibiotic selected from the group consisting of mupirocin vancomycin and neomycin and a combination thereof, and optionally comprises an additional antibiotic selected from the group consisting of polymyxin B, gentamicin, amphotericin B and a combination thereof; and the amino acid comprises a first amino acid selected from the group consisting of a first subcombination of glutamic acid, arginine, and tyrosine, and a second subcombination of serine, aspartic acid, methionine, and alanine, and a combination thereof, and optionally comprises an additional amino acid selected from the group consisting of glycine, histidine, proline, cysteine, valine, isoleucine, leucine, phenylalanine, threonine, lysine, and a combination thereof.

2. The composition according to claim 1, wherein the fatty acid further comprises at least one selected from the group consisting of stearic acid, butyric acid, hexanoic acid, octanoic acid, myristic acid, palmitoleic acid, heptadecanoic acid, eicosanoic acid, and cis-11-eicosenoic acid; wherein, the composition comprises not less than 250 parts of oleic acid, linoleic acid, palmitic acid and linolenic acid.

3. The composition according to claim 2, wherein, in parts by weight, the fatty acid comprises: 20-50 parts of palmitic acid, 10-30 parts of stearic acid, 100-200 parts of oleic acid, 100-300 parts of linoleic acid, 30-50 parts of linolenic acid, 0.1-1 parts of butyric acid, 0.1-1 parts of hexanoic acid, 0.1-1 parts of octanoic acid, 0.1-1 parts of myristic acid, 0.1-1 parts of palmitoleic acid, 0.1-1 parts of heptacarbonic acid, 0.1-1 parts of eicosanoic acid, and 0.3-2 parts of cis-11-eicosaenoic acid.

4. The composition according to claim 1, wherein, in parts by weight, the organic substance comprises: 0.1-10 parts of ellagic acid, 0.1-10 parts of hypaphorine, 0.1-10 parts of huperzine C, 0.1-10 parts of huperzine A, 0.1-10 parts of harmalol, 0.1-10 parts of abrine, 0.1-10 parts of berberine hydrochloride, 0.1-10 parts of 10-gingerol, 0.1-10 parts of methyl gallate, 0.1-10 parts of spathulenol, 0.1-10 parts of 3-furylmethyl 1H-pyrrole-2-carboxylate, 0.1-10 parts of tanshinone, 0.1-10 parts of dihydrocapsaicin, 0.1-10 parts of potassium 7-hydroxy-1-naphthalenesulfonate, 0.1-10 parts of pilocarpine, 0.1-10 parts of adenosine, 0.1-10 parts of firmanoic acid, 0.1-10 parts of glabrolide, 0.1-10 parts of liquidambaric lactone, 0.1-10 parts of schisanlactone, 0.1-10 parts of dehydroepiandrosterone, 0.1-10 parts of 11,13-dehydroivaxillin, 0.1-10 parts of 2-hydroxyzeranolide, 0.1-10 parts of 14,15-beta-dihydroxyklaineanone, 0.1-10 parts of olaquindox, 0.1-10 parts of oridonin, 0.1-10 parts of phorbol, 0.1-10 parts of harmine, 0.1-10 parts of maltol, 0.1-10 parts of hypaconine, 0.1-10 parts of 2-O-rhamnosylicariside II, 0.1-10 parts of theobromine, 0.1-10 parts of theophylline, 0.1-10 parts of hordeine, and 0.1-10 parts of ephedrine.

5. The composition according to claim 1, wherein, in parts by weight, the carbohydrate comprises 0.01-30 parts of glucose and 0.01-30 parts of fructose.

6. The composition according to claim 1, wherein, in parts by weight, the microelement comprises: 0.5-1 parts of calcium, 0.01-0.1 parts of iron, 0.02-0.2 parts of zinc, 0.01-0.2 parts of copper, and 2.5-4 parts of phosphorus.

7. The composition according to claim 1, wherein, in parts by weight, the antibiotic comprises: 0.1-20 parts of mupirocin, 0.1-10 parts of neomycin, 0.1-10 parts of polymyxin B, 0.1-10 parts of gentamicin, 0.1-10 parts of amphotericin B, and 0.1-10 parts of vancomycin.

8. The composition according to claim 1, wherein, in parts by weight, the amino acid comprises: 20-50 parts of glutamic acid, 20-40 parts of arginine, 10-30 parts of aspartic acid, 5-20 parts of serine, 5-20 parts of glycine, 5-20 parts of alanine, 5-20 parts of tyrosine, 1-10 parts of histidine, 1-10 parts of proline, 1-10 parts of cysteine, 5-10 parts of valine, 5-10 parts of isoleucine, 10-30 parts of leucine, 5-20 parts of phenylalanine, 1-5 parts of methionine, 2-15 parts of threonine, and 4-15 parts of lysine.

9. The composition according to claim 1, wherein calcium, iron, zinc, and copper are present in the form of soluble salts comprising calcium gluconate, calcium hydrogen phosphate, calcium lactate, calcium chloride, $FeCl_2 \cdot 4H_2O$, ferrous sulfate, ferrous gluconate, zinc gluconate, zinc sulfate, zinc acetate, copper sulfate, and copper gluconate; and phosphorus is present in the form of phosphates comprising sodium phosphate, disodium hydrogen phosphate, and potassium dihydrogen phosphate.

10. The composition according to claim 9, wherein the composition comprises linoleic acid, ellagic acid, pilocarpine, methyl gallate, glucose, vitamin E, calcium lactate, mupirocin, glutamic acid, arginine, and tyrosine.

11. The composition according to claim 9, wherein the composition comprises oleic acid, linoleic acid, hypaphorine, liquidambaric lactone, oridonin, maltol, glucose, fructose, vitamin E, calcium lactate, potassium dihydrogen phosphate, vancomycin, neomycin, serine, aspartic acid, methionine, and alanine.

12. The composition according to claim 2, wherein the vitamin E is selected from the group consisting of α-tocopherol, β-tocopherol, γ-tocopherol, δ-tocopherol, and any combinations thereof.

13. The composition according to claim 12, wherein the composition comprises palmitic acid, stearic acid, oleic acid, linoleic acid, linolenic acid, butyric acid, hexanoic acid, octanoic acid, myristic acid, palmitoleic acid, heptadecanoic acid, eicosanoic acid, cis-11-eicosaenoic acid, ellagic acid, hypaphorine, huperzine C, huperzine A, harmalol, abrine, berberine hydrochloride, 10-Gingerol, methyl gallate, spathulenol, 3-furylmethyl 1H-pyrrole-2-carboxylate, tanshinone, dihydrocapsaicin, potassium 7-Hydroxy-1-naphthalenesulfonate, pilocarpine, adenosine, firmanoic acid, glabrolide, liquidambaric lactone, schisanlactone, dehydroepiandrosterone, 11,13-dehydroivaxillin, 2-hydroxyedenoid, 14,15-beta-dihydroxyklaineanone, olaquindox, oridonin, phorbol, harmine, maltol, hypaconine, 2-O-rhamnosylicariside II, theobromine, theophylline, hordenine, ephedrine, glucose, fructose, α-tocopherol, β-tocopherol, γ-tocopherol, δ-tocopherol, calcium lactate, ferrous gluconate, zinc gluconate, copper gluconate, disodium phosphate, mupirocin, neomycin, polymyxin B, gentamicin, amphotericin B, vancomycin, glutamic acid, arginine, aspartic acid, serine, glycine, alanine, tyrosine, histidine, proline, cysteine, valine, isoleucine, leucine, phenylalanine, methionine, threonine, and lysine.

* * * * *